(12) United States Patent
Brandon

(10) Patent No.: US 9,928,819 B2
(45) Date of Patent: Mar. 27, 2018

(54) WEARABLE MOVEMENT ALERT SYSTEM

(71) Applicant: Richard Brasco Brandon, Jackson, MS (US)

(72) Inventor: Richard Brasco Brandon, Jackson, MS (US)

(*) Notice: Subject to any disclaimer, the term of this patent is extended or adjusted under 35 U.S.C. 154(b) by 76 days.

(21) Appl. No.: 14/843,246

(22) Filed: Sep. 2, 2015

(65) Prior Publication Data

US 2016/0063982 A1 Mar. 3, 2016

Related U.S. Application Data

(60) Provisional application No. 62/070,711, filed on Sep. 3, 2014.

(51) Int. Cl.
| | |
|---|---|
| *G10K 1/26* | (2006.01) |
| *G10K 1/072* | (2006.01) |
| *A61B 5/00* | (2006.01) |
| *A61B 5/11* | (2006.01) |
| *G10K 1/07* | (2006.01) |
| *G08B 3/10* | (2006.01) |

(52) U.S. Cl.
CPC .............. *G10K 1/26* (2013.01); *A61B 5/1115* (2013.01); *A61B 5/7405* (2013.01); *A61B 5/746* (2013.01); *G10K 1/072* (2013.01); *G08B 3/10* (2013.01); *G10K 1/07* (2013.01)

(58) Field of Classification Search
CPC . G10K 1/07; G10K 1/26; G10K 1/072; G08B 3/10; A61B 5/7405; A61B 5/746; A61B 5/1115

USPC .......... 116/67 R, 137 R, 140, 141, 148, 150, 116/167, 170
See application file for complete search history.

(56) References Cited

U.S. PATENT DOCUMENTS

| | | | | |
|---|---|---|---|---|
| 116,241 | A * | 6/1871 | Volger | G10K 1/071 116/171 |
| 294,184 | A * | 2/1884 | Barton | G10K 1/071 116/171 |
| 530,116 | A * | 12/1894 | Murphy | A63B 43/00 473/571 |
| 870,025 | A * | 11/1907 | Elsas | G10K 1/071 84/406 |
| 1,505,155 | A * | 8/1924 | MacKenzie | G10K 1/071 116/148 |
| 1,528,463 | A * | 3/1925 | Yungk | G10K 1/071 116/148 |
| 1,848,020 | A * | 3/1932 | Merrill | G10K 1/32 116/150 |
| 2,191,683 | A * | 2/1940 | Roberts | A63B 69/3608 116/215 |
| 2,584,223 | A * | 2/1952 | Petelinsek | G10K 1/10 116/150 |

(Continued)

*Primary Examiner* — R. A. Smith
*Assistant Examiner* — Tania Courson
(74) *Attorney, Agent, or Firm* — Jeremy A. Smith; Michael C. Williams; Bradley Arant Boult Cummings LLP

(57) ABSTRACT

The present disclosure provides a wearable movement alert system comprising an enclosure, a divider positioned within the enclosure, a quiet chamber positioned within one longitudinal end of the enclosure, a noise chamber positioned within the longitudinal end of the enclosure that is opposite from the quiet chamber, at least one chime fixed within the noise chamber, and an agitator free to move about within the enclosure.

12 Claims, 5 Drawing Sheets

(56) References Cited

U.S. PATENT DOCUMENTS

| | | | | |
|---|---|---|---|---|
| 2,585,075 A * | 2/1952 | Badovinac | A44C 7/00 | 116/170 |
| 2,598,169 A * | 5/1952 | Hubbell | A63H 5/00 | 116/150 |
| 2,702,521 A * | 2/1955 | Earl | G10K 1/10 | 116/148 |
| 2,787,929 A * | 4/1957 | Musser | G10K 1/071 | 84/406 |
| 3,025,064 A * | 3/1962 | Flood | A63B 69/3608 | 473/211 |
| 3,084,588 A * | 4/1963 | Landon | G10K 1/345 | 116/150 |
| 3,099,245 A * | 7/1963 | Deaner | A42B 1/24 | 116/200 |
| 3,250,243 A * | 5/1966 | Swander, Jr. | G10K 1/068 | 116/151 |
| 3,402,808 A * | 9/1968 | Yannuzzi | A61B 5/117 | 116/67 R |
| 3,703,878 A * | 11/1972 | Badovinac | A44C 7/00 | 116/67 R |
| 3,910,225 A * | 10/1975 | Huber | G10K 1/341 | 116/167 |
| 4,098,509 A * | 7/1978 | Van Krevelen | A63B 69/3608 | 116/148 |
| 4,466,329 A * | 8/1984 | Hayward | G10K 1/36 | 84/406 |
| 4,686,878 A * | 8/1987 | Hebert | G10K 1/10 | 116/141 |
| 5,612,500 A * | 3/1997 | Liang | G10K 1/07 | 116/141 |
| 7,220,904 B2 * | 5/2007 | Rom | G10K 1/08 | 84/402 |
| 7,557,727 B2 * | 7/2009 | Michida | A44B 19/262 | 116/100 |
| 9,240,175 B1 * | 1/2016 | Wyche | G10K 1/10 | |
| 2016/0111074 A1 * | 4/2016 | Lacy | G10K 1/10 | 116/149 |

* cited by examiner

WEARABLE MOVEMENT ALERT SYSTEM

CROSS-REFERENCE TO RELATED APPLICATIONS

This application claims the benefit of, and priority to, U.S. Provisional Application No. 62/070,711 filed Sep. 3, 2014 titled "Walk Alerting and Monitoring Device."

FIELD OF THE INVENTION

The invention relates generally to a system useful for movement notification and more specifically relates to a system particularly useful for alerting a caretaker to a patient's walking movements.

BACKGROUND ART

There are some wearable alert systems currently in place for the elderly. However, most alert systems that now exist for the elderly are one-time, push-button devices that are used in the event of an emergency. In addition, most devices operate on electric or battery power. Therefore, the need exists for a non-electronic system that can be used to alert a patient's caretaker that the patient is up and walking around in a non-emergency situation.

The present invention provides a system which can be operated in non-emergency situations and used to alert a caretaker of a patient's movements. Injuries and other similar incidents can be reduced or prevented because a caretaker hears the audible sounds emitted when a patient is walking and can then find the patient to assist him or her. The present invention also provides a non-electronic alternative so that batteries are not needed. In addition, the present invention only emits sounds when a patient is upright and moving around, but is quiet when the patient is lying down and not at risk of a fall or other similar injury.

SUMMARY OF THE INVENTION

In view of the foregoing shortcomings inherent in the conventional type of methods and systems now present in the prior art, the present invention provides a wearable system for alerting caregivers to a patient's upright movements, even if the patient is not in the caretaker's line of sight. Audible tones are produced from within the system during walking movements, and when the system is in a horizontal position, it remains quiet.

In one embodiment, the wearable movement alert system comprises an enclosure; at least one divider positioned within the enclosure; a quiet chamber positioned within one longitudinal end of the enclosure; a noise chamber positioned within the longitudinal end of the enclosure that is opposite from the quiet chamber, at least one chime fixed within the noise chamber; and an agitator.

In another embodiment, the wearable movement alert system comprises a housing configured to hold internal components; an upper chamber within one end of the housing; a lower chamber within the end of the housing opposite that of the upper chamber; a divider within the housing, wherein the divider separates the upper chamber and the lower chamber such that a channel is formed between the upper chamber and lower chamber; and a plurality of agitators.

Other objects and advantages of the present invention will become obvious to the reader and it is intended that these objects and advantages are within the scope of the present invention.

To the accomplishment of the above and related objects, this invention may be embodied in the form illustrated in the accompanying drawings/pictures, recognizing however, that the drawings are illustrative only, and that changes may be made in the specific construction illustrated and described within the scope of the appended claims.

BRIEF DESCRIPTION OF DRAWINGS

It should be noted that identical features in different drawings are shown with the same reference numeral. Various other objects, features and attendant advantages of the present invention will become fully appreciated as the same becomes better understood when considered in conjunction with the accompanying drawings.

DETAILED DESCRIPTION

Figure 1:
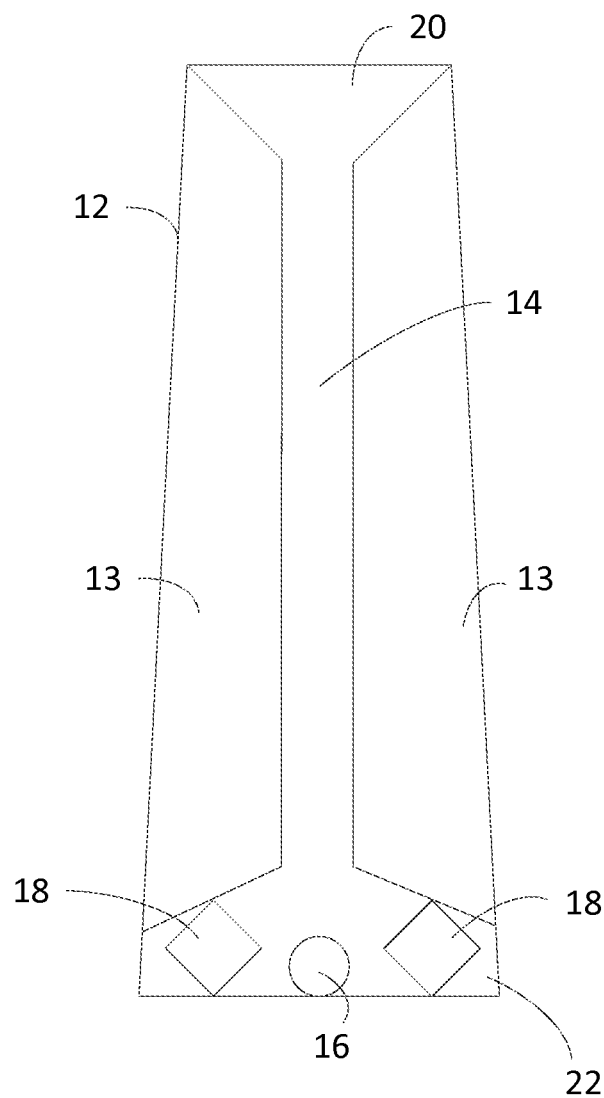
FIG. 1 is a front view of one embodiment of the wearable movement alert system shown in a vertical, upright position.

FIGS. 1 through 5 illustrate various views and embodiments of the present invention. In one embodiment, shown in FIG. 1, the system 10 comprises an enclosure 12 that houses the various internal components of the system 10. The enclosure 12 is shown in a trapezoidal shape, though many different shapes or configurations could be used, such as rectangular, elliptical, cylindrical, conical, and so on. Further, the enclosure 12 may be made of any number of materials, though a type of plastic or other lightweight material may be preferred for added comfort while wearing. The outer portion of the enclosure 12 may include small holes (not shown) or perforations (not shown) in order to allow sound to escape from the system 10 when in use, as further described herein.

Within the enclosure 12, the system 10 comprises a quiet chamber 20 at one end of the enclosure 12, and a noise chamber 22 at the end of the enclosure 12 that is opposite the quiet chamber 20. The quiet chamber 20 and the noise chamber 22 may generally be open or hollow spaces within the enclosure 12. One or more dividers 13 may be included within the enclosure 12 for separating the quiet chamber 20 from the noise chamber 22. The dividers 13 may be solid in nature, or the dividers 13 may comprise a series of walls that separate the two chambers. Generally, the dividers 13 extend from the outer portion of the enclosure 12 toward the center of the enclosure 12, but do not extend so far as to meet in the center of the enclosure 12. Rather, the dividers 13 come together in such a manner as to form a channel 14 leading between the quiet chamber 20 and the noise chamber 22.

One or more chimes 18 may be located within the noise chamber 22. Although FIG. 1 shows two chimes 18, the present invention contemplates using any number of chimes 18, such as 3, 4, 5, 6, 7, 8, 9, or 10. The chimes 18 may be attached to the walls of the enclosure 12 or the walls of the dividers 13, or may be attached to both. The chimes 18 may be permanently fixed or removably attached within the noise chamber 22, but in any event are configured in such a way that they remain within the noise chamber 22 no matter how the system 10 is moved, turned, or positioned.

The chimes 18 may be small, cymbal-like structures made of metal or other material, though a type of metal may be preferred so that the chimes 18 are more likely to generate sound when in contact with the agitator 16. Other configurations may be used, such as tubes, rods, or bells.

The system 10 also comprises at least one agitator 16. The agitator 16 remains unfixed to any surfaces and free to move internally about the system 10. In this manner, the channel 14 is wide enough to allow the agitator 16 to pass through and travel between the quiet chamber 20 and the noise chamber 22, as further described below. The agitator 16 is shown as a spherical object, though other configurations could be used. However, a spherical shape may generally assist the agitator 16 in moving easily within the system 10 because it is capable of a smooth, rolling motion. Many types of materials may be used to fabricate the agitator 16, such as metal, plastic, or wood. Depending on the structure and material of the chimes 18, the agitator 16 should be comprised of a material that facilitates sound generation when it comes into contact with the chimes 18. Because the agitator 16 is free to move about the system 10, a walking motion causes the agitator 16 to move between and make alternating contact with the chimes 18, thus causing sound emission.

Figure 2:
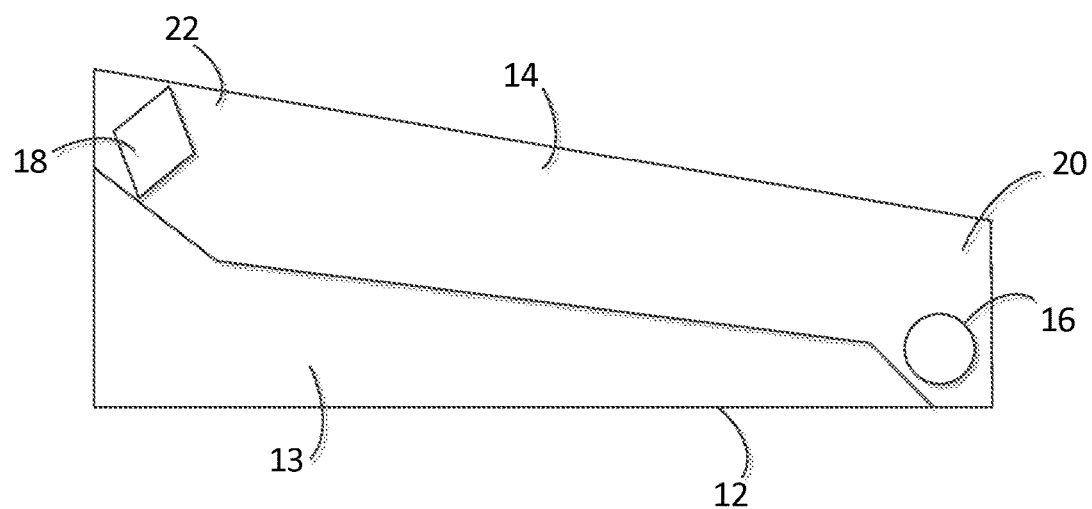
FIG. 2 is a side view of one embodiment of the wearable movement alert system shown in a horizontal position.

FIG. 2 is an alternate view of the embodiment shown in FIG. 1, and further illustrates the function of the present invention. In FIG. 2, the system 10 is shown from the side, in a horizontal position. Generally, the noise chamber 22 is configured to be higher than the quiet chamber 20 when the system 10 is in a horizontal position, thus allowing gravity to cause the agitator 16 to either move to or remain in the quiet chamber 20. For example, if the agitator 16 had been in the noise chamber 22, when the system 10 is turned on its side, the agitator 16 would then move through the channel 14 toward the quiet chamber 20, where it would come to rest. The angle and slope of the dividers 13, and thus the angle and slope of the channel 14, are configured to direct the agitator 16 away from the noise chamber 22 by using gravity. Conversely, when the system 10 is moved into an upright or vertical position, the agitator 16 is again pulled by gravity through the channel 14 and into the noise chamber 22, as shown in FIG. 1. The downward angle of the channel 14 allows the system 10 to remain quiet when the wearer is lying down, and only make noise when the wearer is upright and walking.

Figure 3:
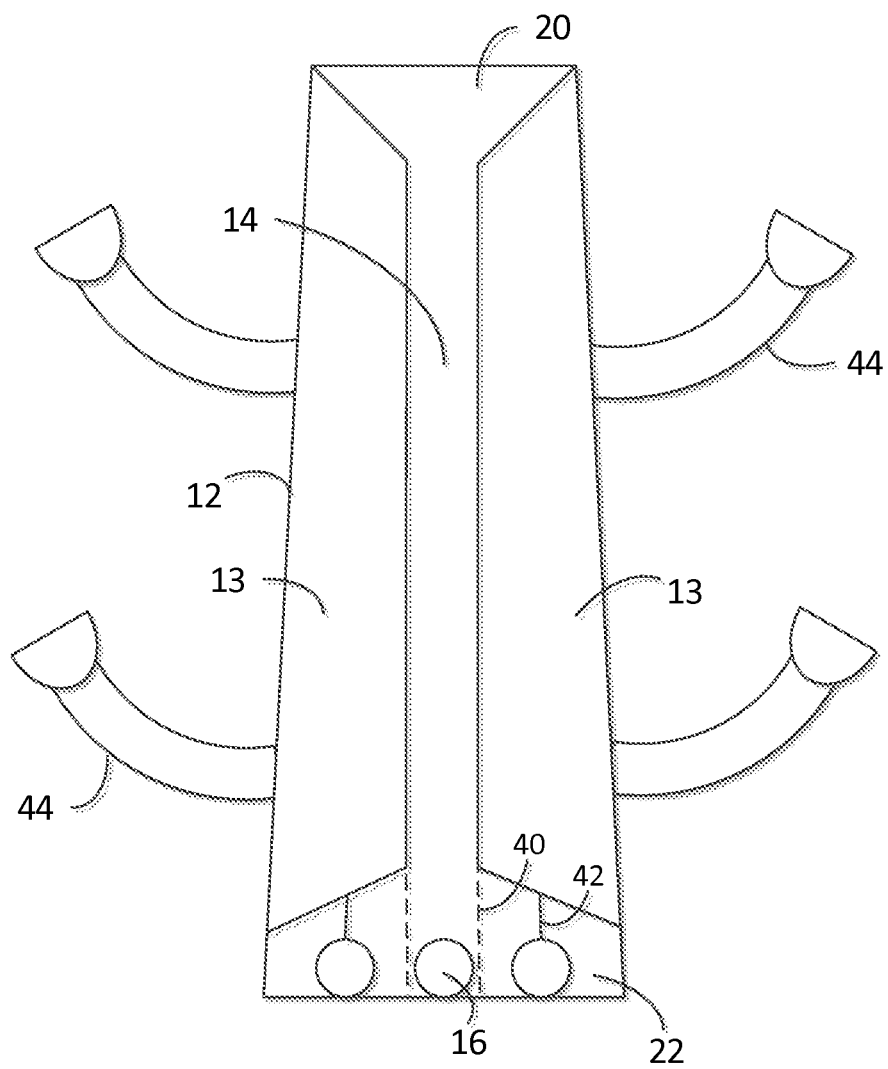
FIG. 3 is a front view of an alternative embodiment of the wearable movement alert system, shown in a vertical, upright position.

FIG. 3 shows an alternative embodiment of the system 10. In this embodiment, multiple agitators 16 are used in place of chimes 18. At least one agitator 16 is configured to remain in the noise chamber 22, and may be permanently fixed within the noise chamber or may be removably attached. In this manner, a suspension thread 42 may be used to hold the agitator 16 in place within the noise chamber 22. Still, at least one agitator 16 remains unfixed to any surface and free to move about the system 10.

In operation of the system 10, the free agitator 16 moves to the noise chamber 22 when the system 10 is in an upright position, as described above in reference to FIG. 2. The free agitator 16 comes into contact with the agitators 16 in the noise chamber 22 to generate sound. Alternatively, the agitators 16 that remain within the noise chamber 22 may be held in place by the use of separation screens 40, rather than suspension thread 42. The separation screens 40 may be configured to prevent some of the agitators 16 from leaving the noise chamber 22 when the system 10 is positioned on its side, and instead only allow the free agitator 16 to do so. However, the separation screens 40 comprise a sheer material that allows the agitators 16 to make noise when they come into contact with one another, even through the separation screen 40 material.

FIG. 3 also shows the use of attachment straps 44, which the wearer may use to fasten the system 10 to himself or herself. The attachment straps 44 may be made of a variety of materials, including nylon, leather, cloth, elastic, or other fabric. In addition, the attachment straps 44 may utilize a wide variety of fasteners for attaching to a patient's clothing, including VELCRO, buckles, or clips. Although FIG. 3 shows the use of four attachment straps 44, any number of attachment straps 44 may be used. Alternatively, a clip (not shown) may be affixed to the system 10 and used to fasten the system 10 to a patient, similar to clips used to fasten a device to one's belt. The present invention contemplates that a number of fastening devices may be used with any of the embodiments shown or described herein.

Figure 4:
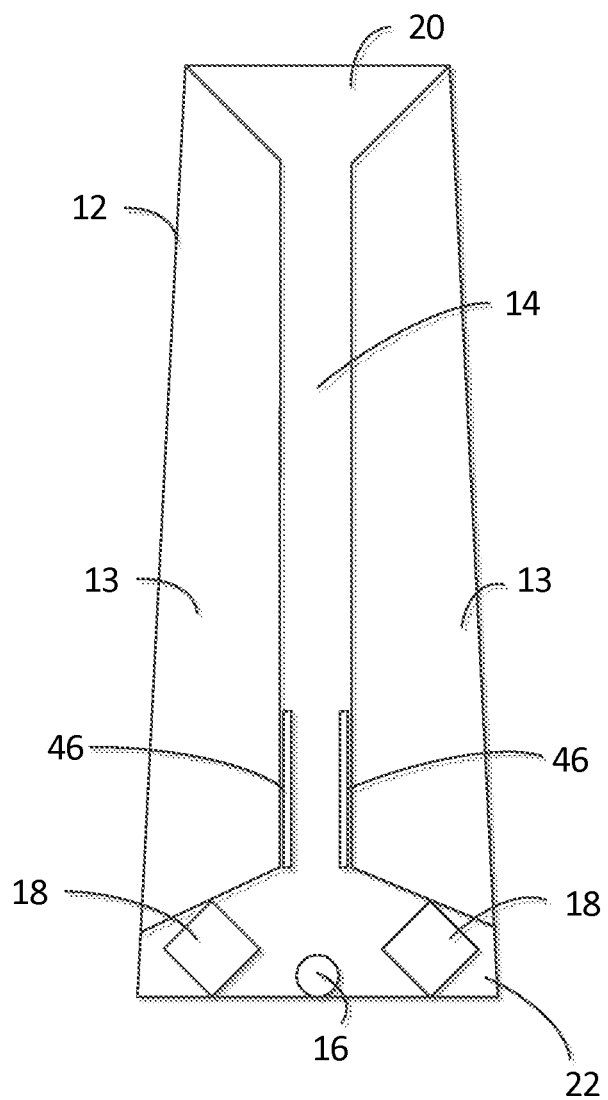
FIG. 4 is a front view of an alternative embodiment of the wearable movement alert system, shown in a vertical, upright position.

FIG. 4 shows an alternative embodiment of the system 10. In this embodiment, inhibitors 46 may be included to dampen sounds, making the sounds more muffled or preventing sounds altogether, depending on user preference. The inhibitors 46 may include one or more movable walls which may slide from a position in the channel 14 to a position in the noise chamber 22, as described in reference to FIG. 5 below. FIG. 4 shows the inhibitors 46 in a disengaged position, at rest in the channel 14. In this position, the inhibitors 46 allow the agitator 16 to reach the noise chamber 22 and come into contact with the chimes 18, thus generating sound. The inhibitors 46 may be attached to a handle (not shown) or switch (not shown) on the outside of the enclosure 12, so that a user may move the handle (not shown) or switch (not shown) to an "on" or "off" position, thus engaging or disengaging the inhibitors 46 within the enclosure 12.

Although two inhibitors 46 are shown in FIG. 4, the present invention contemplates that other numbers of inhibitors 46 can be used. For example, one inhibitor 46 may be used to simply muffle the overall sound of the system 10. Alternatively, two inhibitors 46 may be used as shown in order to completely prevent sound generation. In addition, the inhibitors 46 may be used with other embodiments of the present invention, such as an embodiment with multiple agitators 16 and no chimes 18, as described in reference to FIG. 3 above.

Figure 5:
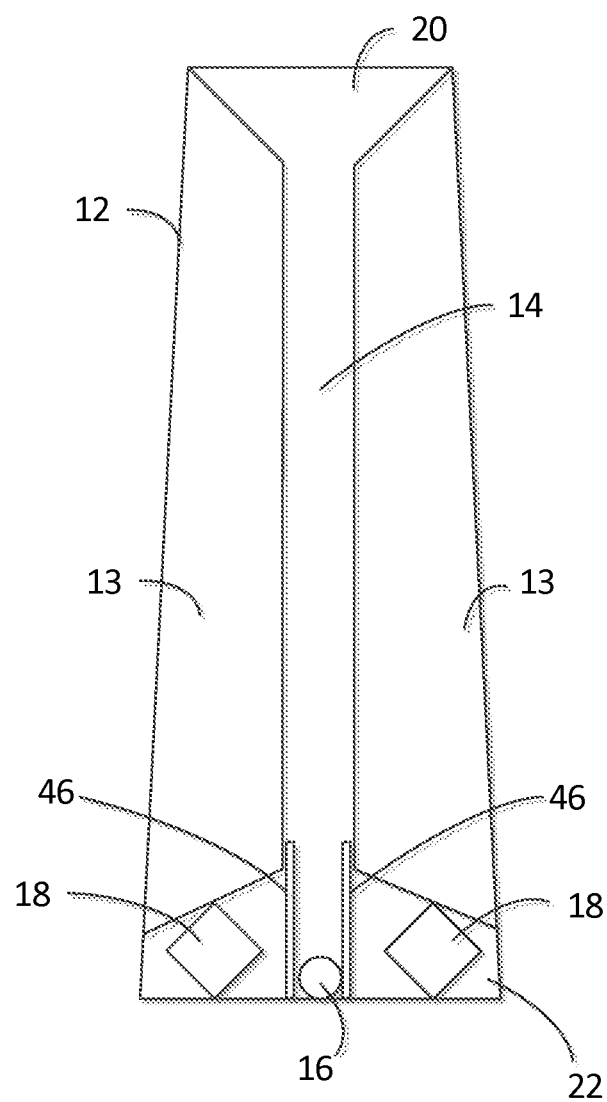
FIG. 5 is a front view of an alternative embodiment of the wearable movement alert system, shown in a vertical, upright position with the inhibitor in a closed configuration.

FIG. 5 shows an alternative embodiment of the system 10. In this embodiment, the inhibitors 46 are shown in an engaged position, within the noise chamber 22. In this position, the inhibitors 46 act as a barrier and do not allow the agitator 16 to come into contact with the chimes 18. As a result, no sound would be generated, even though the system 10 may be in an upright and vertical configuration. As noted above, the inhibitors 46 may be attached to a handle (not shown) or switch (not shown) on the outside portion of the enclosure 12, so that a user may manually slide the inhibitors 46 downward from a disengaged position within the channel 14 to an engaged position within the noise chamber 22.

While the invention has been discussed as being useful in the care of an elderly person, it should be recognized that the system 10 can be used for other purposes, such as the care of mentally impaired or otherwise incapacitated individuals, or children. The system 10 may be used in a number of settings, such as home or hospice care or other institutional settings.

What is claimed is:

1. A wearable movement alert system comprising:
   a. an enclosure;
   b. at least one divider positioned within the enclosure extending the length of the enclosure;
   c. a quiet chamber positioned within one longitudinal end of the enclosure;
   d. a noise chamber positioned within the longitudinal end of the enclosure that is opposite from the quiet chamber;
   e. at least one chime fixed within the noise chamber; and
   f. an agitator;
   wherein the agitator translates between the noise and quiet chamber.

2. The wearable movement alert system of claim 1 further comprising a channel,
   wherein the channel is formed within the enclosure by the divider; and
   wherein the channel connects the quiet chamber and the noise chamber at a horizontal angle such that the channel forms a downward slope from the noise chamber to the quiet chamber.

3. The wearable movement alert system of claim 2, further comprising at least one attachment strap,
   wherein the attachment strap is permanently fixed to the outer portion of the enclosure.

4. The wearable movement alert system of claim 2, further comprising a clip,
   wherein the clip is permanently fixed to the outer portion of the enclosure.

5. The wearable movement alert system of claim 1, further comprising an inhibitor
   wherein the inhibitor comprises a wall that is configured to move between a position within the channel and a position within the noise chamber.

6. A wearable movement alert system wearable movement alert system comprising:
   a. a housing configured to hold internal components;
   b. a quiet chamber within one end of the housing;
   c. a noise chamber within the end of the housing opposite that of the quiet chamber;
   d. a divider within the housing that extends from the length of the housing, wherein the divider separates the quiet chamber and the noise chamber such that a channel is formed between the quiet chamber and noise chamber; and
   e. a plurality of agitators;
   wherein one or more agitators translate between the quiet and noise chambers.

7. The wearable movement alert system of claim 6,
   wherein the channel connects the quiet chamber and the noise chamber at a horizontal angle such that the channel forms a downward slope from the quiet chamber to the noise chamber.

8. The wearable movement alert system of claim 7, further comprising at least one suspension thread,
   wherein one end of the suspension thread is attached to a wall of the quiet chamber, and
   wherein the other end of the suspension thread is attached to an agitator, such that the agitator will remain in the quiet chamber.

9. The wearable movement alert system of claim 7, further comprising at least one separation screen,
   wherein the separation screen is attached to the walls of the quiet chamber, and
   wherein the separation screen is positioned such that it prevents an agitator from leaving the quiet chamber and moving into the channel.

10. The wearable movement alert system of claim 7, further comprising at least one attachment strap,
    wherein the attachment strap is permanently fixed to the outer portion of the enclosure.

11. The wearable movement alert system of claim 7, further comprising a clip,
    wherein the clip is permanently fixed to the outer portion of the enclosure.

12. The wearable movement alert system of claim 7, further comprising an inhibitor
    wherein the inhibitor comprises a wall that is configured to move between a position within the channel and a position within the quiet chamber.

* * * * *